United States Patent [19]
Grutzner

[11] Patent Number: 5,662,472
[45] Date of Patent: Sep. 2, 1997

[54] HUE AND LIGHTNESS IDENTIFICATION SYSTEM FOR DENTAL PRODUCTS

[75] Inventor: Andreas Grutzner, Reichenan, Germany

[73] Assignee: Dentsply GmbH, Germany

[21] Appl. No.: 516,594

[22] Filed: Aug. 18, 1995

[51] Int. Cl.[6] .................................................. A61C 5/04
[52] U.S. Cl. ............................................................ 433/90
[58] Field of Search .............................. 433/89, 90, 26; 206/63.5, 571, 364, 368, 369

[56] References Cited

U.S. PATENT DOCUMENTS

| | | | |
|---|---|---|---|
| 716,676 | 12/1902 | Cruttenden . | |
| 921,015 | 5/1909 | Skinner . | |
| 1,188,417 | 5/1916 | Dalbey . | |
| 1,306,816 | 6/1919 | Howard . | |
| 1,775,329 | 9/1930 | Sprague . | |
| 2,102,591 | 12/1937 | Hagemeier | 128/236 |
| 2,251,206 | 7/1941 | Rutrough | 32/60 |
| 2,708,438 | 5/1955 | Cohen | 128/220 |
| 2,754,590 | 9/1956 | Cohen | 32/60 |
| 2,837,824 | 3/1958 | Moller | 32/60 |
| 2,841,145 | 7/1958 | Epps | 128/218 |
| 2,847,009 | 8/1958 | Blease | 128/222 |
| 2,869,543 | 1/1959 | Ratcliff et al. | 128/218 |
| 3,052,239 | 9/1962 | Silver et al. | 128/218 |
| 3,052,240 | 9/1962 | Silver et al. | 128/218 |
| 3,089,489 | 5/1963 | Dunmire | 128/216 |
| 3,093,133 | 6/1963 | Everett | 128/216 |
| 3,098,483 | 7/1963 | Nielsen | 128/220 |
| 3,100,045 | 8/1963 | Via, Jr. | 206/47 |
| 3,164,303 | 1/1965 | Trautmann | 222/190 |
| 3,220,412 | 11/1965 | McConnaughey | 128/218 |
| 3,326,215 | 6/1967 | Sarnoff et al. | 128/218 |
| 3,373,743 | 3/1968 | Saffir | 128/218 |
| 3,417,971 | 12/1968 | Blank et al. | 259/37 |
| 3,477,432 | 11/1969 | Shaw | 128/218 |
| 3,494,359 | 2/1970 | Zackheim | 128/218 |
| 3,521,356 | 7/1970 | Newman | 32/60 |
| 3,534,735 | 10/1970 | Sly | 128/220 |
| 3,557,787 | 1/1971 | Cohen | 128/220 |
| 3,575,318 | 4/1971 | Kunz | 222/79 |
| 3,581,399 | 6/1971 | Dragan | 32/60 |
| 3,612,352 | 10/1971 | Smith | 222/1 |
| 3,638,314 | 2/1972 | Lopez et al. | 32/60 |
| 3,684,136 | 8/1972 | Baumann | 222/386 |
| 3,724,077 | 4/1973 | Preston et al. | 32/60 |
| 3,738,066 | 6/1973 | Panetti | 51/178 |
| 3,739,947 | 6/1973 | Baumann et al. | 222/136 |
| 3,756,571 | 9/1973 | Winberg | 259/60 |
| 3,828,434 | 8/1974 | Mosch | 32/60 |
| 3,831,742 | 8/1974 | Gardella et al. | 206/219 |
| 3,890,713 | 6/1975 | Nielsen | 32/60 |
| 3,900,954 | 8/1975 | Dragan | 32/60 |

(List continued on next page.)

FOREIGN PATENT DOCUMENTS

| | | |
|---|---|---|
| 1 255 126 | 6/1989 | Canada . |
| 0 382 481 | 8/1990 | European Pat. Off. . |
| WO 94/18905 | 9/1994 | WIPO . |

*Primary Examiner*—Nicholas D. Lucchesi
*Attorney, Agent, or Firm*—Dale R. Lovercheck; James B. Bieber

[57] ABSTRACT

A system for identification of hue and lightness of dental products formed from dental material within enclosures comprises an alpha series of at least three caps (A) having an alpha cap hue and supported by enclosures enclosing dental materials which are polymerizable to form an alpha series of dental products having an alpha product hue. The system includes a beta series of at least three caps (B) having a beta cap hue supported by enclosures enclosing dental materials which are polymerizable to form dental products having a beta product hue. The system includes a first series of at least three caps (1) having a first cap lightness and each of said first caps being supported by an enclosure enclosing a dental material which is polymerizable to form a dental product having a first product lightness. The system includes a second series of at least three caps (2) having a second cap lightness, and each of said second caps being supported by an enclosure enclosing a dental material which is polymerizable to form a dental product having a second product lightness.

19 Claims, 5 Drawing Sheets

U.S. PATENT DOCUMENTS

| | | | |
|---|---|---|---|
| 3,917,062 | 11/1975 | Winters | 206/219 |
| 3,951,387 | 4/1976 | Warden et al. | 259/67 |
| 4,023,675 | 5/1977 | Claasen | 206/219 |
| 4,084,320 | 4/1978 | Skeirik | 32/60 |
| 4,189,756 | 2/1980 | Dragan | 360/14 |
| 4,330,280 | 5/1982 | Dougherty et al. | 433/90 |
| 4,373,632 | 2/1983 | VanZandt | 206/457 |
| 4,384,853 | 5/1983 | Welsh | 433/90 |
| 4,391,590 | 7/1983 | Dougherty | 433/90 |
| 4,392,590 | 7/1983 | Hofmann-Igl | 222/174 |
| 4,693,706 | 9/1987 | Ennis, III | 604/87 |
| 4,828,117 | 5/1989 | Panzera et al. | 206/63.5 |
| 4,883,180 | 11/1989 | Humphrey et al. | 206/534 |
| 4,969,816 | 11/1990 | Drumm | 433/90 |
| 5,083,921 | 1/1992 | Dragan | 433/90 |
| 5,199,567 | 4/1993 | Discko, Jr. | 206/369 |
| 5,289,919 | 3/1994 | Fischer | 206/571 |
| 5,364,267 | 11/1994 | Fischer et al. | 433/90 X |
| 5,464,348 | 11/1995 | Fischer et al. | 433/90 X |

HUE AND LIGHTNESS IDENTIFICATION SYSTEM FOR DENTAL PRODUCTS

The invention relates to hue and lightness identification systems for dental products. Improved hue and lightness identification is provided in accordance with the invention by a system of rationally colored enclosure bodies and caps which identify the hue and lightness of the dental product formed from the material enclosed in each enclosure. The enclosures are for example, dispensing cartridges.

As the shade of the tooth substance varies among individuals, among the teeth of a single person and even in different parts of the same tooth, modern restorative materials are offered in a selection of shades. To select the appropriate shade, the dentist normally uses the shade guide provided with the product. It is made of samples of the restorative material or other suitable resins. Thus, reference between shade guide and restorative material is made by a numeric, alphabetic or color code printed on both shade guide and packaging of the restorative. For example, the Vita shade system consists of the four basic color groups A: reddish-brown, B: reddish yellow, C: gray and D: reddish-gray. Each color group has our shades. As a rule, the darkness of the shades increases within every group, i.e. A1, B1, C1, D2 are light shades, and A4, B4, C4, D4 are dark shades. The reference teeth of the Vita shade guide may be arranged according to shade groups or according to the degree of lightness.

In a color cap system for restorative material in enclosures previously used by Caulk Division of Dentsply International only two yellow and two gray lightness were included along with one white lightness, one brown lightness and one other lightness.

Cruttenden in U.S. Pat. No. 716,676 discloses dental cement injector. Kelley in U.S. Pat. No. Des. 742,446 discloses dental filling tool. Skinner in U.S. Pat. No. 921,015 discloses root canal filling dental injector. Dalbey in U.S. Pat. No. 1,188,417 discloses dental instrument. Sprague in U.S. Pat. No. 1,775,329 discloses applicator. Howard in U.S. Pat. No. 1,306,816 discloses syringe for injecting cement in teeth. Hagemeier in U.S. Pat. No. 2,102,591 discloses dental syringe. Rutrough in U.S. Pat. No. 2,251,206 discloses amalgam carrier. Boeger U.S. Pat. No. 2,505,028 discloses syringe for applying heat-fluent impression composition to dental inlay preparations and the like, and impression-material cartridge for use therein. Cohen in U.S. Pat. No. 2,708,438 discloses hypodermic syringe. Cohen in U.S. Pat. No. 2,754,590 discloses container for toothache remedy. Moller in U.S. Pat. No. 2,837,824 discloses amalgam carrier and ejector. Epps in U.S. Pat. No. 2,841,145 discloses syringe. Blease in U.S. Pat. No. 2,847,009 discloses dispensing liquids. Ratcliff et al. in U.S. Pat. No. 2,869,543 discloses injector. Silver et al. in U.S. Pat. No. 3,052,239 discloses disposable hypodermic syringe. Silver et al. in U.S. Pat. No. 3,052,240 discloses disposable hypodermic syringe. Dunmire in U.S. Pat. No. 3,089,489 discloses aspirating type hypodermic syringes. Everett in U.S. Pat. No. 3,093,133 discloses hypodermic apparatus. Nielsen in U.S. Pat. No. 3,098,483 discloses two-compartment hypodermic syringe for separate storing of more components. Via, Jr. in U.S. Pat. No. 3,100,045 discloses mixing containers. Trautmann in U.S. Pat. No. 3,164,303 discloses storage and mixing cartridge. McConnaughey et al. in U.S. Pat. No. 3,220,412 discloses holder for hypodermic syringe cartridges. Sarnoff et al. in U.S. Pat. No. 3,326,215 discloses two compartment syringe with vapor seal between compartments. Saffir in U.S. Pat. No. 3,373,743 discloses disposable hypodermic syringe. Blank et al. in U.S. Pat. No. 3,417,971 discloses mixing and ejection tool. Shaw in U.S. Pat. No. 3,477,432 discloses combination mixing and injecting medical syringe. Zackheim in U.S. Pat. No. 3,494,359 discloses two compartment syringe with a single barrel. Newman in U.S. Pat. No. 3,521,356 discloses dispenser for dental filling material. Sly in U.S. Pat. No. 3,534,735 discloses disposable injector and holder. Cohen in U.S. Pat. No. 3,557,787 discloses disposable syringe. Kunz in U.S. Pat. No. 3,575,318 discloses water pistol. Dragan in U.S. Pat. No. 3,581,399 discloses composite resin filling syringe and technique. Smith in U.S. Pat. No. 3,612,352 discloses amalgam cartridge and method of making same and method and apparatus for dispensing amalgam from a cartridge. Lopez et al. in U.S. Pat. No. 3,638,314 discloses amalgam carrier and dispenser with preload capsule. Baumann in U.S. Pat. No. 3,684,136 discloses receptacle having a dividing wall. Preston et al. in U.S. Pat. No. 3,724,077 discloses mixing syringe. Lopez et al. in U.S. Pat. No. 3,738,066 discloses dental impression material injecting syringe. Baumann et al. in U.S. Pat. No. 3,739,947 discloses storing and mixing receptacle. Winberg in U.S. Pat. No. 3,756,571 discloses mixing capsule in particular for dental preparation. Mosch in U.S. Pat. No. 3,828,434 discloses mixing capsule. Gardella et al. in U.S. Pat. No. 3,831,742 discloses dental mixing capsule. Nielsen in U.S. Pat. No. 3,890,713 discloses dental devices. Dragan in U.S. Pat. No. 3,900,954 discloses dental filling gun and nozzle tip therefor. Winters in U.S. Pat. No. 3,917,062 disclose mixing container for for dental materials. Warden et al. in U.S. Pat. No. 3,951,387 discloses cartridge for storing and mixing at least two independent ingredients. Claasen in U.S. Pat. No. 4,023,675 discloses packing for impression material for dental use. Skeirik in U.S. Pat. No. 4,084,320 discloses system for mixing and dispensing dental amalgam. Dragan in U.S. Pat. No. 4,189,756 discloses manual extruder. Dougherty et al. in U.S. Pat. No. 4,330,280 discloses ejector holder for capsule-like cartridge. VanZandt in U.S. Pat. No. 4,373,632 disclose nail polish hanger. Welsh in U.S. Pat. No. B1 4,384,853 disclose ejector holder for capsule-like cartridge. Dougherty in U.S. Pat. Nos. 4,391,590 and B1 4,391,590 disclose cartridge for viscous material. Hofmann-Igl in U.S. Pat. No. 4,392,590 discloses eye drop dispensing bottle. Ennis, III in U.S. Pat. No. 4,693,706 disclose two compartment mixing syringe. Panzera et al in U.S. Pat. No. 4,828,117 disclose porcelain dental restoration having a plurality of uniform, color-matched layers. Drumm in U.S. Pat. No. 4,969,816 disclose dental material carrier and applicator. Doscki, Jr. in U.S. Pat. No. 5,199,567 disclose single patient dose dental cartridge tray and orgainizing system. Fischer in U.S. Pat. No. 5,289,919 disclose endodontic dental kit with color-coding means. Fischer in U.S. Pat. No. 5,364,267 disclose syringe system for matching tooth composite colors.

It is an object of the present invention to provide a rational system for identification of the hue and lightness of dental material enclosed in an enclosure.

Shad is sometimes used herein to mean hue.

Details of the foregoing objects and of the invention, as well as other objects thereof, are set forth in the following specification and illustrated in the accompanying drawings comprising a part thereof.

BRIEF DESCRIPTION OF THE INVENTION

A system is provided for identification of hue and lightness of dental products formed from dental material within enclosures an alpha series of at least three caps (A) having an alpha cap hue and supported by enclosures enclosing dental materials which are polymerizable to form an alpha series of dental products having an alpha product hue. The system includes a first series of at least three caps (B) having a beta cap hue supported by enclosures enclosing dental materials which are polymerizable to form dental products having a beta product hue.

The system includes a first series of at least three caps (1) having a first cap lightness and each said first caps being supported by an enclosure enclosing a dental material which is polymerizable to form a dental product having a first product lightness.

The system includes a second series of at least three caps (2) having a second cap lightness, and each of the said second caps being supported by an enclosure enclosing a dental material which is polymerizable to form a dental product having a second product lightness. The beta cap hue is more reddish-yellow than alpha cap hue. The beta product hue is more reddish-yellow than the alpha product hue. The alpha cap hue is more reddish-brown than the beta cap hue. The alpha product hue is more reddish-brown than the beta product hue. The second cap lightness is darker than the first cap lightness. The second product lightness is darker than the first product lightness. The difference in hue between the alpha cap hue and the beta cap hue is substantially greater than the difference in hue between the alpha product hue and the beta product hue, and the difference in lightness between the first cap lightness and the second cap lightness is substantially greater than the difference in lightness between the first product lightness and the second product lightness.

DETAILED DESCRIPTION OF THE PREFERRED EMBODIMENT

Cartridge caps are small, and are used on single-dosed containers which allow the direct placement of the restorative material into natural dental tooth cavities. Some prior art caps have an imprint on the cartridge body stating the respective shade. This information is, however, difficult to read, as the code has to be printed in small letters to match the size of the cartridge.

In accordance with the invention the restorative contained in the cartridge is identified by the color of the cap, and the alpha-numeric shade codes on the body of the cartridge. The packaging for cartridges filled with A shades have a reddish color symbol. The packaging for cartridges filled with B shades bears a yellowish color symbol. Those with C shades have a grayish and those with D shades have a brownish symbol. In the case of light shades, the color symbol is of a light color, e.g. the color symbol of B1 is light yellow. Dark shades are identified by a dark color code, e.g. A4 bears a dark-red color code.

The color indicator of the invention makes a direct citation of a reference color standard. The color indicator on the packaging indicates to the dentist the color type and lightness/darkness of the material in the cartridge.

Color type identifies whether the material is reddish (A), yellowish (B), grayish (C) or brownish (D). Lightness/darkness of the material is indicated by the lightness/darkness of the color indicator. "Pastel" colors refer to light shades, "intensive" color symbols refer to dark shades.

Cartridges may be easily and logically placed in an organizer. The invention permits the easy arrangement of cartridge caps and shade guide according to both shade type (A–D) and lightness.

The color of a restorative material, which is shaded, for example, according to the Vita Lumin® Vacuum shade system, is described by a color code relating directly to the shade character (color type and lightness) of the material. Yellowish indicators refer to yellowish restoratives. Grayish indicators refer to greet restoratives and so on. Pastel colors refer to light shades, intensive color symbols refer to dark shades.

The system is primarily meant to identify the shades contained in cartridge caps in combination with an imprint on the cartridge body.

The invention is now described with reference to FIGS. 1A through 11. Cartridges may be supported in lows and columns by a support S. A system is provided for identification of hue and lightness of dental products formed from dental material within enclosures. An alpha series of at least three caps having an alpha cap hue and supported by enclosures enclosing dental materials which are polymerizable to form an alpha series of dental products having an alpha product hue. As shown in FIG. 1A an alpha series of caps includes caps A1, A2, A3, A3.5 and A4 supported by enclosures BA1, BA2, BA3, BA3.5 and BA4 respectively.

The system includes a beta series of at least three caps having a beta cap hue supported by enclosures enclosing dental materials which are polymerizable to form dental products having a beta product hue. As shown in FIG. 1A a beta series of caps includes caps B1, B2, B3 and B4 supported by enclosures BB1, BB2, BB3 and BB4 respectively.

The system includes a first series of at least three caps having a first cap lightness and each of the first caps is supported by an enclosure enclosing a dental material which is polymerizable to form a dental product having a first product lightness. As shown in FIG. 1A a first series of caps includes caps A1, B1 and C1 supported by enclosures BA1, BB1 and BC1 respectively.

The system includes a second series of at least three caps having a second cap lightness, and each of the second caps being supported by an enclosure enclosing a dental material which is polymerizable to form a dental product having a second product lightness. As shown in FIG. 1A a second series of caps includes caps A2, B2 and C2 supported by enclosures BA2, BB2 and BC2 respectively.

The beta cap hue is more reddish-yellow than the alpha cap hue. The beta product hue is more reddish-yellow than the alpha product hue. The alpha cap hue is more reddish-brown than the beta cap hue. The alpha product hue is more reddish-brown than the beta product hue. The second cap lightness is darker than the first cap lightness. The second product lightness is darker than the first product lightness. The difference in hue between the alpha cap hue and the beta cap hue is substantially greater than the difference in the hue between the alpha product hue and the beta product hue, and the difference in lightness between the first cap lightness and the second cap lightness is substantially greater than the difference in lightness between the first product lightness and the second product lightness.

Figure 1:
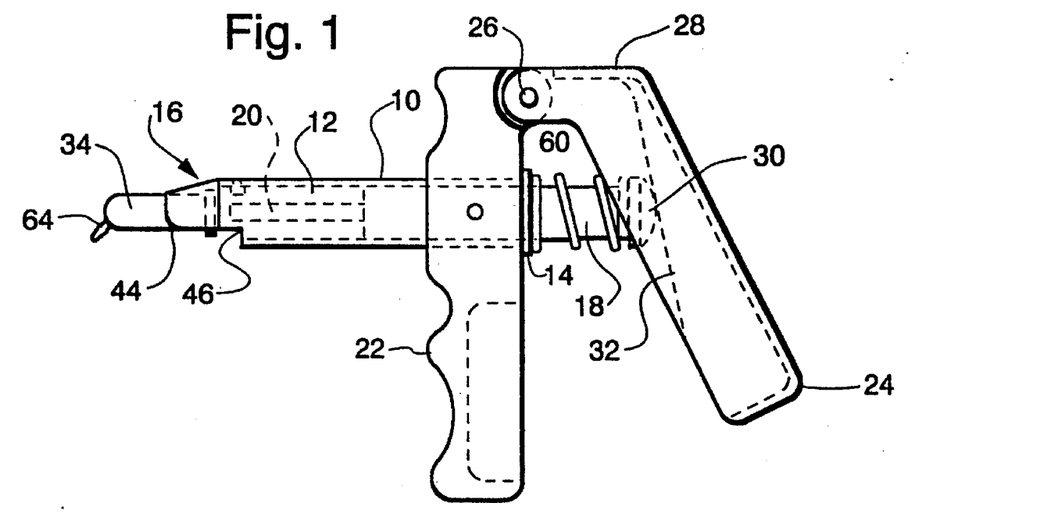
FIG. 1 is a side elevation of an ejector holder for supporting a cartridge in accordance with the present invention.
Figure 1A:
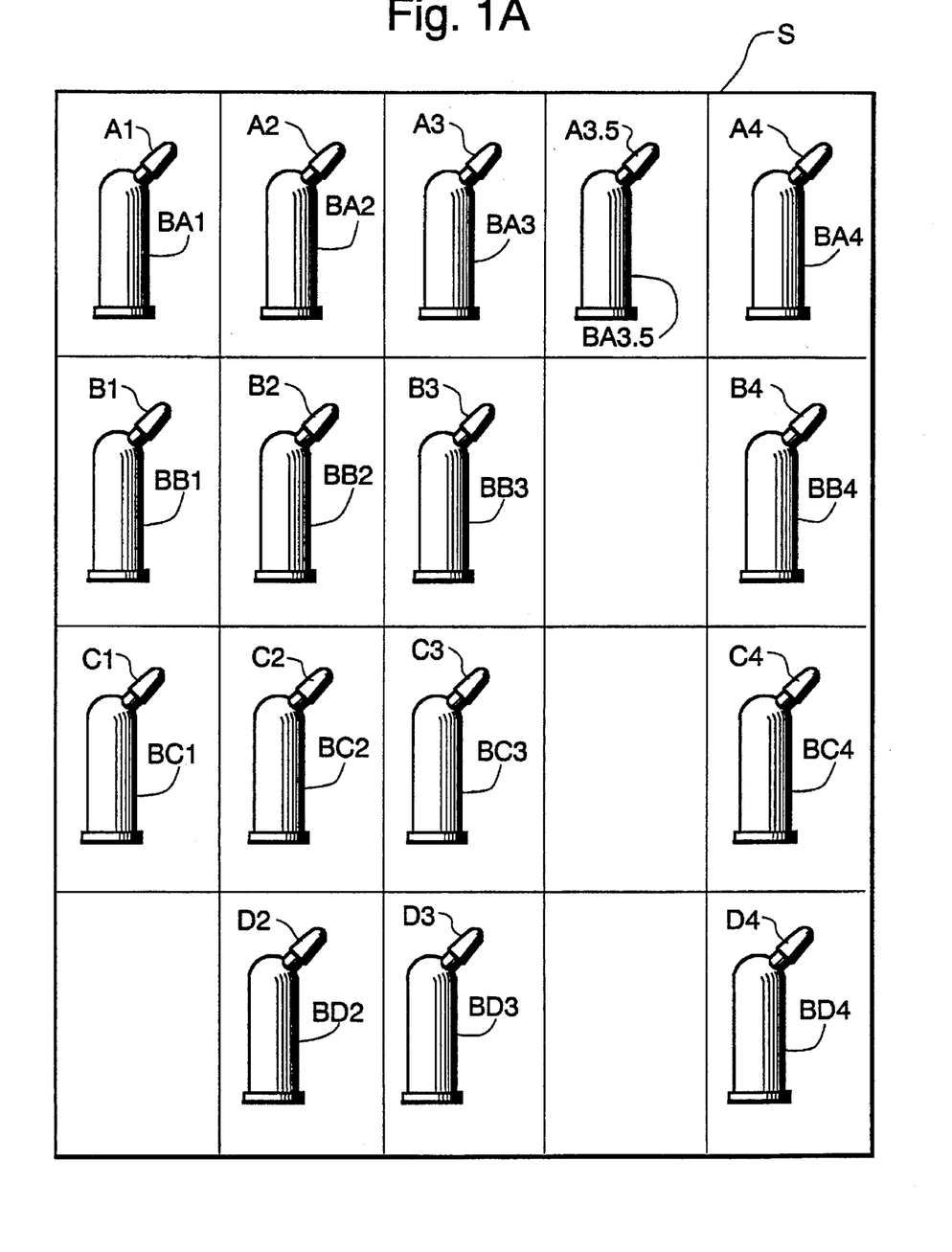
FIG. 1A is a schematic view of a system of cartridges with caps in accordance with the present invention.

FIG. 1 shows an ejector holder to hold in operative position a cartridge from the hue and lightness identification system of the present invention. The holder comprises a barrel 10 having a interior bore 12 extending from the rearward end 14 of the barrel toward the forward end 16 thereof for purposes of receiving a plunger 18 of the same diameter as that of the interior bore 12 for the major portion of the length of the plunger, the forward end of the plunger having a smaller diameter extension 20.

The rearward end 14 of the barrel 10 extends through and is fixed to a handle member 22 with which the barrel 10 is perpendicular. Pivotally connected to the handle 22 is an operating lever 24, the upper end of which is pivotally connected to the upper end of handle 22 by a pivot pin 26. The upper end 28 of operating lever 24 is offset laterally to facilitate operation of the lever 24 with respect to the outer end of plunger 18 which terminates in a button 30 engageable by the inner surface 32 of operating lever 24.

Figure 2:
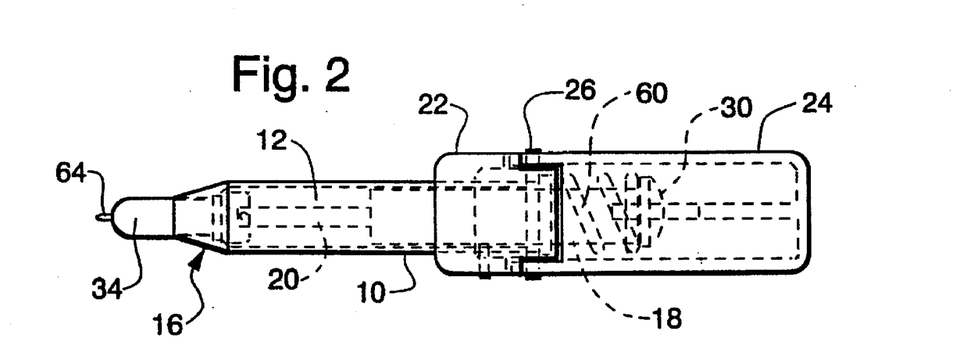
FIG. 2 is a top plan view of the holder and cartridge shown in FIG. 1.
Figure 3:
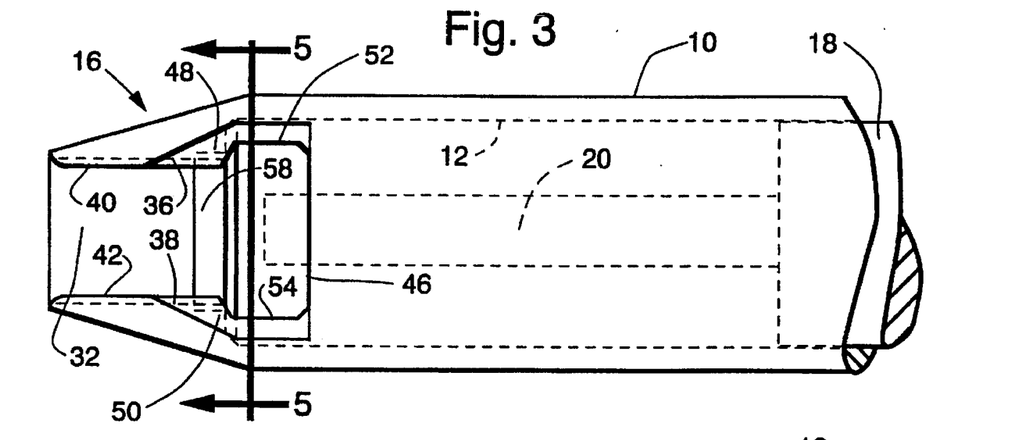
FIG. 3 is a fragmentary enlarged bottom plan view of the forward end of the barrel of the ejector holder shown in FIGS. 1 and 2.
Figure 4:
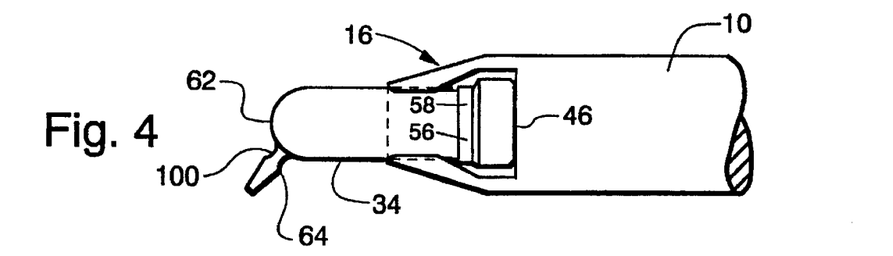
FIG. 4 is a fragmentary bottom plan view of the ejector holder similar to FIG. 3, but on a smaller scale, and illustrating a cartridge supported in the forward end of the barrel.

With more particular reference to FIGS. 1–4 it is seen that the forward end 16 of the barrel 10 is tapered and is provided with a longitudinally extending opening comprising compartment 32 which extends rearwardly from the terminal end of the forward end 16 toward the interior bore 12. The lower surface of compartment 32, as viewed in FIG. 3, is semi-cylindrical and is complementary to the elongated body of cartridge 34 so as to receive and seat the same, as shown in FIGS. 1, 2 and 4. However, the sidewalls 36 and 38 of compartment 32 extend upwardly from the semi-cylindrical bottom surface shown in FIG. 3 and are parallel to each other for a limited distance and the upper edges 40 and 42 extend toward each other a limited distance. The uppermost portions of sidewalls 36 and 38 also have limited flexibility, whereby the distance between the upper edges 40 and 42 of said sidewalls is slightly less than the diameter of the cartridge 34, whereby there is a snap-acting retaining function provided by said sidewalls and the upper edges 40 and 42 with respect to the cartridge 34 when the latter is inserted in the compartment 32.

Figure 5:
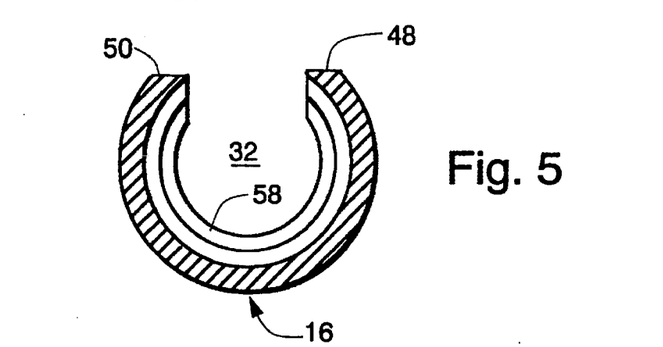
FIG. 5 is a vertical sectional view of the forward end portion of the barrel of the ejector holder shown in FIG. 3, as seen on the line 5—5 thereof.
Figure 6:
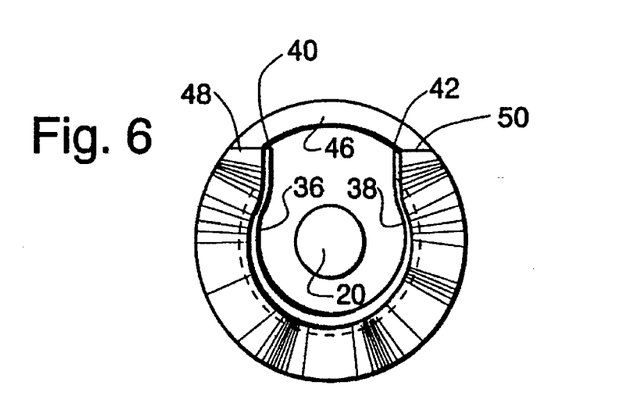
FIG. 6 is a front end view of the forward end of the barrel shown in FIGS. 1–4.

The forward end 16 of the barrel 10 also has a cutaway portion 44 extending longitudinally rearward to form a shoulder 46, which determines the inner end of the cutaway portion. Due to the fact that the forward end 16 is tapered and the barrel 10 otherwise is circular, the cutaway arrangement provides flat surfaces 48 and 50. Also, as best shown in FIG. 3, the sidewalls of the compartment 32, at the inner ends thereof, have lateral recesses 52 and 54 which are spaced apart a greater distance than the diameter of the annular exterior flange 56 in order to permit the insertion of the flange into compartment 32 which, following radial insertion movement thereof into the compartment, the cartridge may be moved axially forward for disposition of the flange 56 in an undercut seat 58, which is clearly shown in FIGS. 3–5. The seat, in conjunction with the portion of the compartment 32 extending forwardly therefrom, provides a firm means for supporting a cartridge 34, which is retained seated in the compartment, especially by means of the snap-fitting arrangement provided by the upper edges 40 and 42 of the sidewalls 36 and 38, as described hereinabove.

Without restriction thereto, the preferred material from which the barrel 10, handle member 22 and operating lever 24 are formed is a suitable rigid plastic material in order that these elements may be formed readily and accurately by molding from raw plastic material; obviously, the coiled spring 60 is formed from spring wire for purposes of retracting the plunger 18 when the operating lever 24 is released, following an ejection of material from the cartridge 34.

Figure 7:
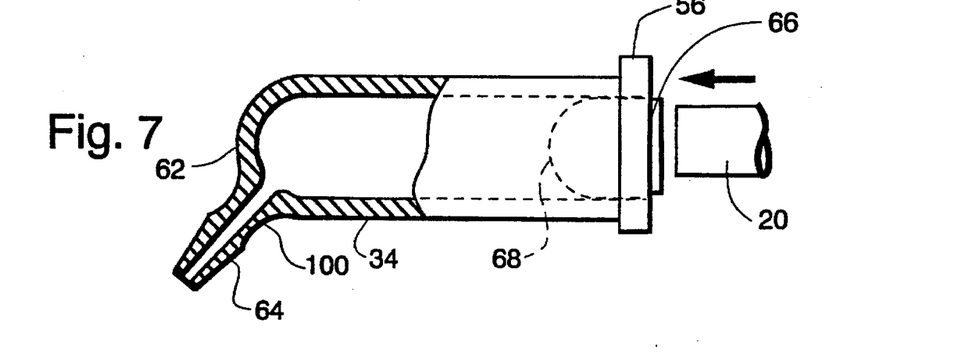
FIG. 7 is a side elevation, partly broken away, of a cartridge similar to that shown in FIGS. 1, 2 and 4, but on a larger scale, and illustrating a piston inserted in the open end of the cartridge and also showing fragmentarily a portion of a plunger rod of the ejector holder adapted to engage the piston of the cartridge.

The cartridge 34 which comprises the subject of the instant application is also preferably formed by molding from appropriate rigid synthetic resin or plastic material by means of a suitable mold. The intermediate body portion of the capsule 34 is of uniform interior and exterior diameter and extends from annular flange 56 adjacent the open end of the cartridge to the opposite closed end 62. The body portion is cylindrical, whereas the closed end 62 is preferably hemispherical but is provided with an angularly extending discharge nipple 64, the opening of which is preferably a very fine dimension of small diameter. To effect ejection of material from the cartridge 34, such as dental filling material, cement, or other viscous dental material and the like, for example, the cartridge 34 includes a piston 66, which is very closely complementary in diameter to the interior of the cartridge 34, and the inner end 68 thereof also is hemispherical and complementary to the interior of the closed end 62 of the cartridge. Without restriction thereto, the outer end of the piston may be flat for engagement, for example, with the extension 20, shown fragmentarily in FIG. 7, when the plunger 18 is moved forwardly by actuation of the operating lever 24.

Removal of the capsule 34 from the compartment 32 is accomplished readily by snapping the cartridge outwardly beyond the somewhat flexible upper edges 40 and 42 of the compartment after the contents within the cartridge have been discharged or exhausted, as required.

From the foregoing, it will be seen that the ejector holder is especially adapted to receive the particular type of cartridge to be used therewith, which is the subject of the instant application. The ejector is of very simple, highly effective design, to permit sure and quick mounting of the cartridge within the compartment in the forward end of the barrel of the holder and, with equal facility, removal of the cartridge therefrom is readily achieved.

The cartridge comprising the invention not only is capable of serving as a receptacle for material to be discharged when filled, for example, from a storage supply, but, even more importantly, the cartridge can be filled at a factory with predetermined quantities of material, by automatic machinery, and sealed therein by application of the piston 66, which, under the circumstance, serves as a closure for the cartridge. The above-described design particularly facilitates such operations. Further, during filling, air in the cartridge in advance of the material can be discharged through the nipple 64 until filled and then the open end of the nipple may suitably and inexpensively be closed by suitable seal means, such as a small piece of sheet material having pressure-sensitive cement on one side and fold said piece across the nipple in any suitable manner.

Figure 8:
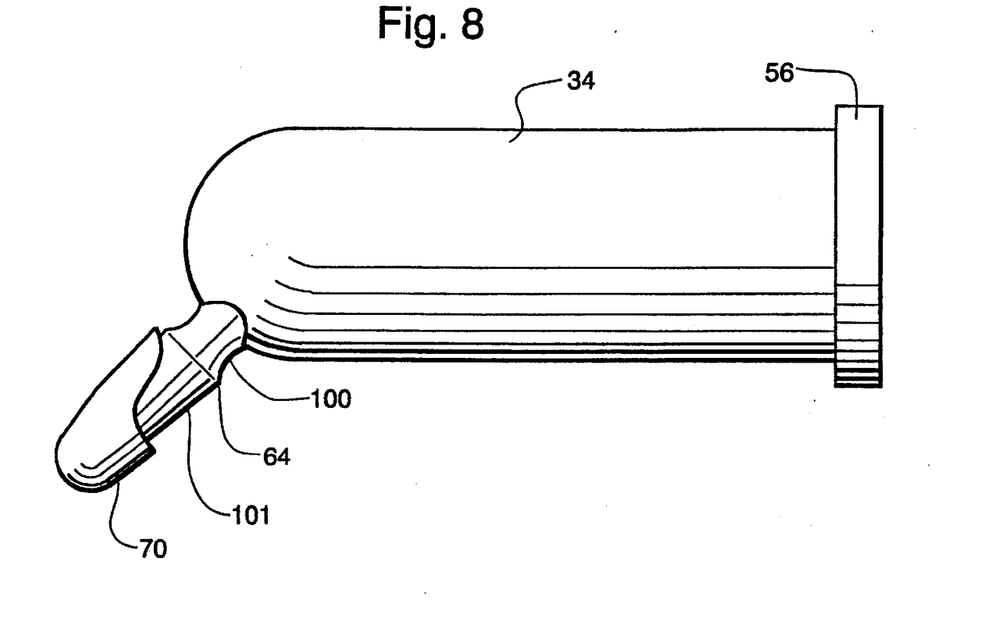
FIG. 8 is a side elevation of a cartridge similar to FIG. 7, partially showing a cap over the discharge nipple of the cartridge body.
Figure 9:
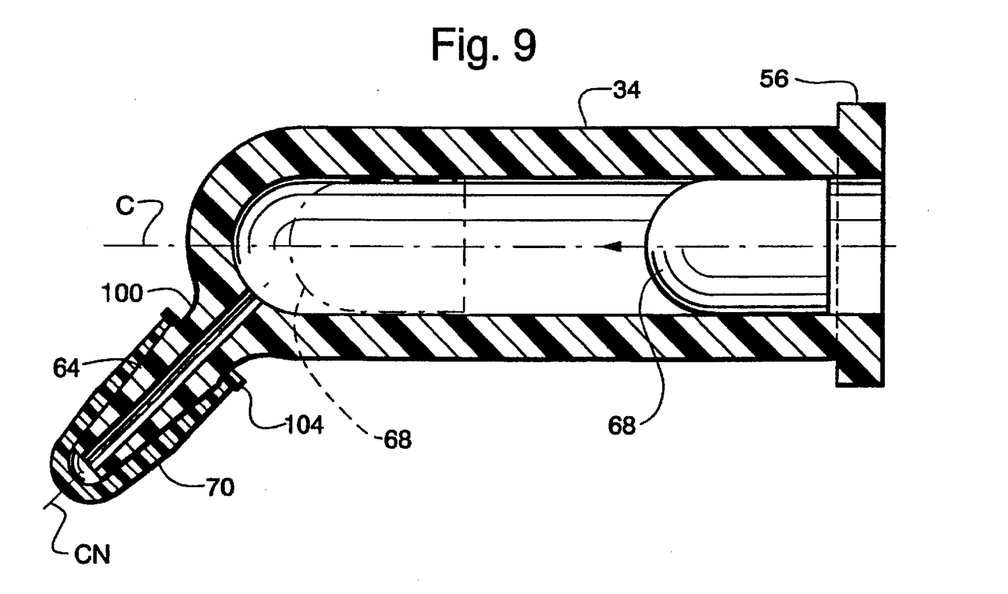
FIG. 9 is a vertical section of the cartridge shown in FIG. 8.

In accordance with the invention, a further improved feature for the cartridge comprises providing a preferably cup-shaped cap 70 which is suitably shaped either to frictionally engage the tip portion of the nipple 64, or either the cap or nipple, or both, to secure the cap releasably upon the tip of the nipple in sealed manner. Cap 70 has outer flange 104 positioned adjacent to the opening of cap 70. In closed position, the inner surface of cap 70 is snap-fit to the outer surface of nipple 64. Cap 70 is retained by the nipple in a closed position, and force sufficient to slightly bend the wall of the cap is required to initially move the cap away from body of cartridge 32 along nipple 64 from the closed position.

Moreover, the cap 70 serves an important additional possible feature in that, in addition to sealing the contents of the cartridge, in conjunction with the piston 66, the cap also may be color-coded for any a number of purposes such as to indicate the kind of material for specified purposes, weight or quantity of the material therein, setting time, and otherwise.

Also, the body of the cartridge as well as the cap 70 and piston 66 may all be molded from similar plastic material which is colored suitably to render the items opaque or otherwise impervious to the transmission of ambient light which, if the contents are subject to being set by such light, prevents premature setting thereof.

Thus, in accordance with a preferred embodiment, the invention provides a miniature capsule-like cartridge having a hollow elongated generally cylindrical body having an inner wall with a substantially uniform diameter. The body has a central axis C as shown in FIG. 9. The inner wall encloses a chamber. One end of the body is open and formed at the extremity thereof with an annular circular exterior flange. The opposite end of the body is closed by an end wall. A discharge integrally connected to the body and has a passageway therethrough extending from the chamber at the closed end of the body to facilitate discharge from the cartridge. The nipple has an outer wall. The outer wall has a proximal diameter 100 proximal to the body and a medial diameter 101 at a position medial to the body. The medial diameter is greater than the proximal diameter. Preferably the proximal diameter is at least 5 percent less than the medial diameter. The nipple has a central axis CN. A cup-shaped cap is removably connected to the discharge nipple on the body to close the outer end of the nipple. The cap extends over the medial position of the nipple.

Figure 10:
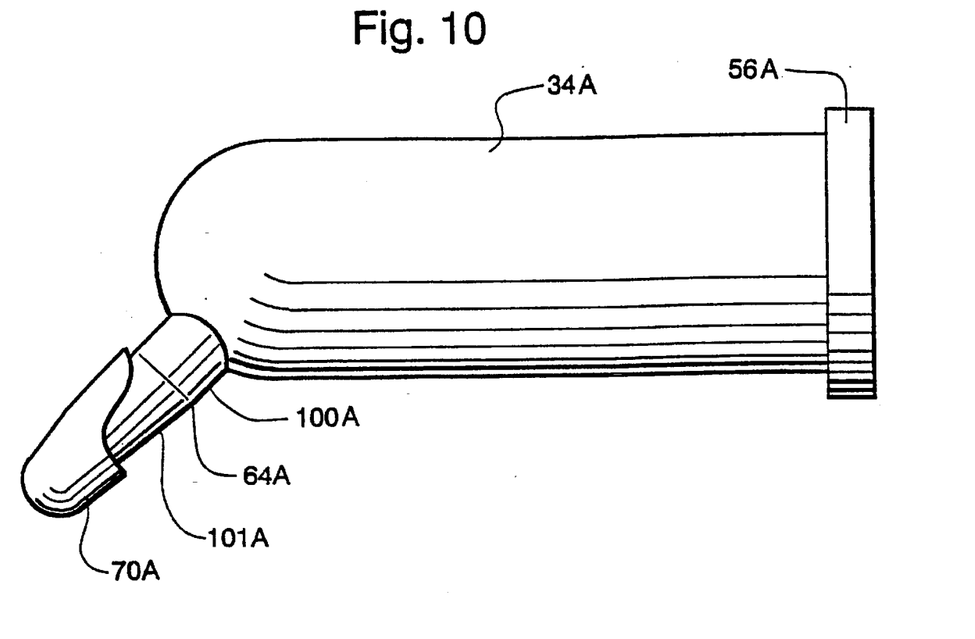
FIG. 10 is a side elevation of a preferred cartridge in accordance with the invention.
Figure 11:
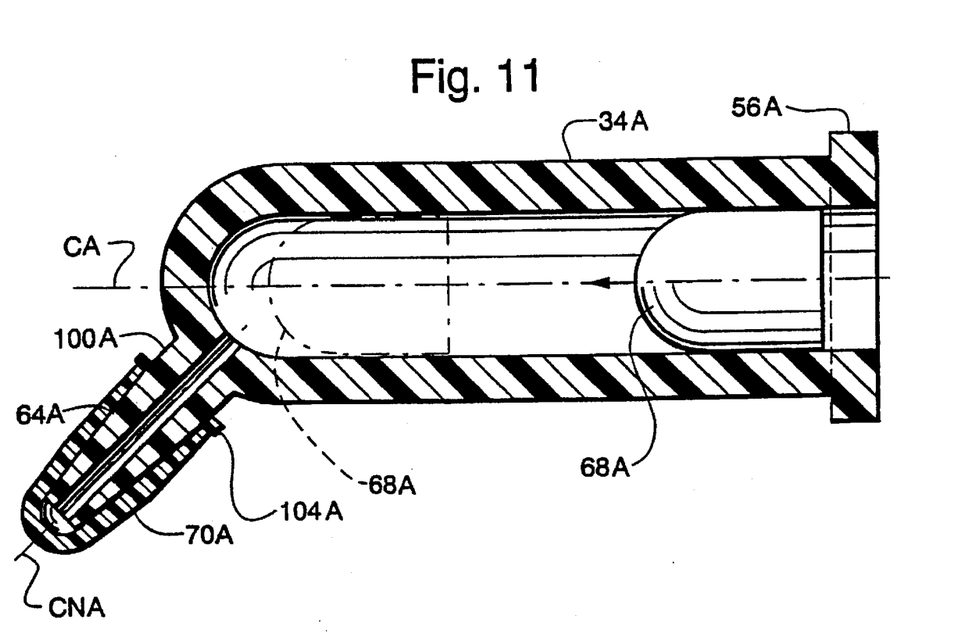
FIG. 11 is a vertical section of the cartridge shown in FIG. 10.

As shown in FIGS. 10 and 11, cartridge 34A in accordance with the invention has a flange 56A and a piston with an inner end 68A. Cartridge 34A is used in the same manner as described above for cartridge 34 with the holder having barrel 10. Preferably cup-shaped cap 70A is suitably shaped either to frictionally engage the tip portion of the nipple 64A, or either the cap or nipple, or both, to secure the cap releasably upon the tip of the nipple in sealed manner. Cap 70A has outer flange 104A positioned adjacent to the opening of cap 70A. In closed position, the inner surface of cap 70A is snap-fit to the outer surface of nipple 64A. Cap 70A is retained by the nipple in a closed position, and force sufficient to slightly bend the wall of the cap is required to initially move the cap away from body of cartridge 34A along nipple 64A from the closed position.

Moreover, the cap 70A serves an important additional possible feature in that, in addition to sealing the contents of the cartridge, in conjunction with the piston, the cap also may be color-coded for any a number of purposes such as to indicate the kind of material for specified purposes, weight or quantity of the material therein, setting time, and otherwise.

Thus, in accordance with a preferred embodiment, the invention provides a miniature capsule-like cartridge having a hollow elongated generally cylindrical body having an inner wall with a substantially uniform diameter. The body has a central axis CA as shown in FIG. 11. The inner wall encloses a chamber. One end of the body is open and formed at the extremity thereof with an annular circular exterior flange. The opposite end of the body is closed by an end wall. A discharge integrally connected to the body and has a passageway therethrough extending from the chamber at the closed end of the body to facilitate discharge from the cartridge. The nipple has a flange 104A and an outer wall. The outer wall has a proximal diameter 100A proximal to the body and a medial diameter 101A at a position medial to the body. The medial diameter is equal to the proximal diameter. The nipple has a central axis CNA. A cup-shaped cap is removably connected to the discharge nipple on the body to close the outer end of the nipple. The cap extends over the medial position of the nipple.

Preferably, the cartridge includes a piston having sidewalls closely complementary to the inner walls of the body and inserted into the open end thereof. The inner end of the piston is complementary in shape to the interior surface of the closed end of the body. Preferably the cap has an inner wall, and the inner wall of the cap engages the outer wall of the nipple at the medial portion of the nipple. Preferably the body has a planar surface positioned adjacent to the closed end and opposite to the nipple and the planar surface intersects the end wall along a line which forms an acute angle to the central axis of the body. Preferably the acute angle is between 3 degrees and 25 degrees.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

What is claimed is:

1. A system for identification of hue and lightness of dental products formed from dental material within enclosures, comprising:

an alpha series of at least three caps (A) having an alpha cap hue and supported by enclosures enclosing dental materials which are polymerizable to form an alpha series of dental products having a first product hue, a beta series of at least three caps (B) having a beta cap hue supported by enclosures enclosing dental materials which are polymerizable to form dental products having a beta product hue, a first series of at least three caps (1) having a first cap lightness and each of said first caps being supported by an enclosure enclosing a dental material which is polymerizable to form a dental product having a first product lightness, a second series of at least three caps (2) having a second cap lightness, and each of said second caps being supported by an enclosure enclosing a dental material which is polymerizable to form a dental product having a second product lightness, said beta cap hue being more reddish-yellow than said alpha cap hue, said beta product hue being more reddish-yellow than said alpha product hue, said alpha cap hue being more reddish-brown than said beta cap hue, said alpha product hue being more reddish-brown than said beta product hue, said second cap lightness being darker than said first cap lightness, said second product lightness being darker than said first product lightness the difference in hue between said alpha cap hue and said beta cap hue being substantially greater than the difference in hue between said alpha product hue and said beta product hue, and the difference in lightness between said first cap lightness and said second cap lightness being substantially greater than the difference in the lightness between said first product lightness and second product lightness.

2. The system of claim 1 further comprising a chi series of caps (C) having a chi cap hue and supported by enclosures enclosing dental materials which are polymerizable to form a chi series of dental products having a chi product hue, and wherein the difference in hue between said alpha cap hue and said beta cap hue is greater than the difference in hue between said alpha product hue and said chi product hue.

3. The system of claim 2 further comprising a third series of caps (3) having a third cap lightness, and each of said third caps being supported by an enclosure enclosing a dental material which is polymerizable to form a dental product having a third product lightness, and wherein the difference in lightness between said first cap lightness and said second cap lightness is greater than the difference in lightness between said first product lightness and said third product lightness.

4. A system of claim 1 wherein said alpha cap hue is reddish brown.

5. The system of claim 4 wherein each said enclosure comprises a miniature cartridge, having:

a hollow elongated generally cylindrical body having an inner wall with a substantially uniform diameter, said inner wall enclosing dental material in a chamber, one end of said body being open and formed at the extremity thereof with an annular circular exterior flange, the opposite end of said body being closed by an end wall, said dental material being adapted to form a dental product having a characteristic shade, said body having an outer surface with an alphanumeric indication of the said shade, a discharge integrally connected to said body and having a passageway therethrough extending from said chamber at said closed end of said body to facilitate discharge from the cartridge, said nipple having a wall.

6. The system of claim 1 wherein said beta cap hue is reddish yellow.

7. The system of claim 1 wherein each said chi cap hue is gray.

8. The system according to claim 7 further characterized by said body and piston being formed from plastic material suitably colored to render the same impervious to the transmission of ambient light, thereby rendering the cartridge adapted to contain light-curable material and the like in a manner to prevent premature curing of such material while stored in such cartridge.

9. The system of claim 7 wherein said nipple outer wall has a distal diameter and a medial diameter, and said medial diameter is greater than said distal diameter.

10. The system of claim 9 wherein each said cap has an inner surface, and said inner surface of each said cap is snap-fit to said outer surface of a respective said nipple.

11. The system of claim 9 wherein each said cap is retained by a respective nipple in a closed position, and force sufficient to slightly bend said wall of said cap is required to initially move said cap away from said body along said nipple.

12. The system of claim 9 wherein said nipple has a wall, said wall having an outer surface with a proximal diameter proximal to said body and a medial diameter medial to said body, said medial diameter being greater than or equal to said proximal diameter.

13. The system of claim 7 wherein said body has a flat portion opposite to said nipple and adjacent to said closed end.

14. The system of claim 1 further comprising a delta series of at least three caps (d) having a delta cap hue and supported by enclosures enclosing dental materials which are polymerizable to form a delta series of dental products having d delta product hue.

15. The system of claim 1 wherein each said enclosure is a cartridge comprising:

a hollow elongated uniformly cylindrical body of predetermined length and uniform diameter interiorly and exteriorly and molded from rigid plastic material, one end of said body being open and formed at the extremity thereof with an annular relatively short circular exterior flange of limited width and adapted to be detachably mounted within a complementary seat in an ejector type holder, the opposite end of said body being closed by a wall of substantially the same uniform thickness as said body, said body enclosing said polymerizable dental material, a discharge nipple of the same material as the body and molded integrally therewith and having a passage therethrough extending from said closed end of said body to facilitate directing discharge from the cartridge to the interior of an oral cavity, a piston having sidewalls closely complementary to the inner walls of said body and inserted into the open end thereof to form a combination closure and ejecting means for said material contained in said cartridge, the inner end of said piston being hemispherical and complementary in shape to the interior surface of the closed end of said body to effect ejection of substantially the entire contents of said cartridge when said piston is fully inserted into said body of the cartridge.

16. The system of claim 1 further comprising a delta cap having a hue which is reddish-gray.

17. The system of claim 1 wherein said dental material enclosed within any one of said enclosure has a total mass of less than 500 grams.

18. The system of claim 1 wherein said dental material enclosed within any one of said enclosures has a total mass of less than 100 grams.

19. The system of claim 1 wherein said dental material enclosed within any one of said enclosures has a total mass of less than 50 grams.

* * * * *